Figure 1:
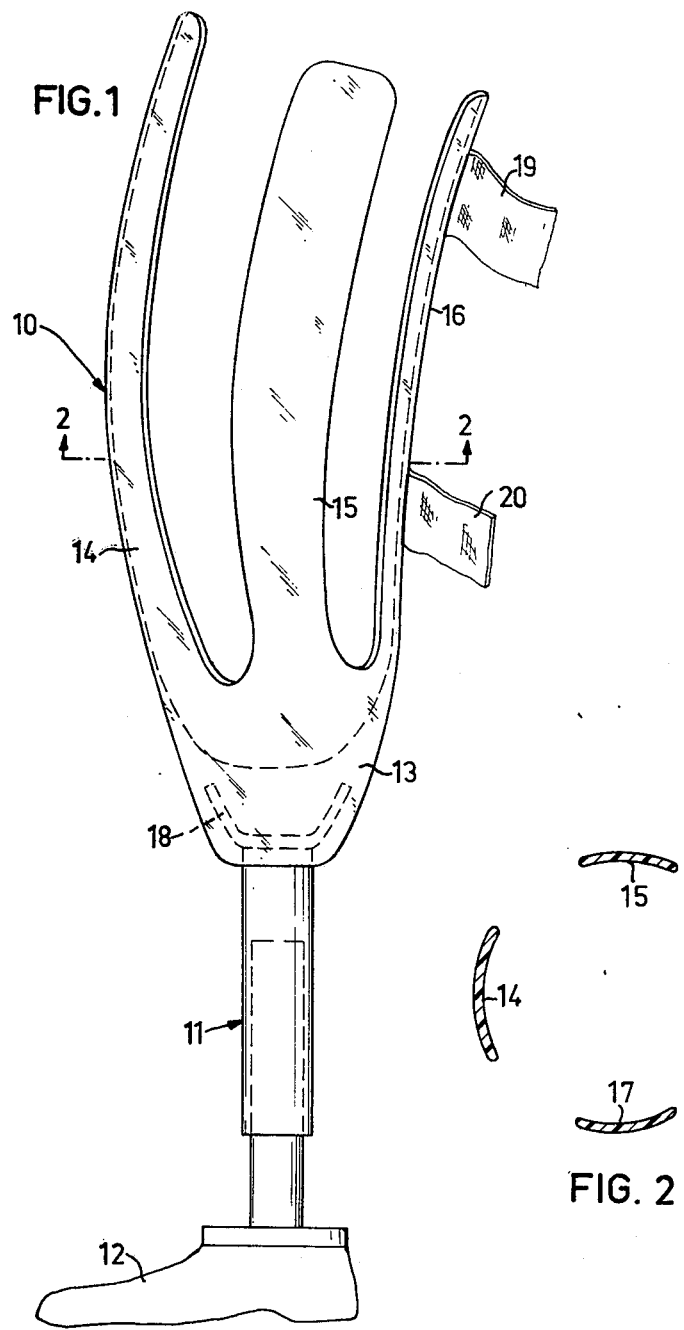

United States Patent [19]

Marsh et al.

[11] 4,128,903
[45] Dec. 12, 1978

[54] TEMPORARY WALKING AID FOR USE AFTER LOWER LEG AMPUTATIONS

[75] Inventors: Gunnar Marsh, Karlskrona; Ole Henrikssen, Asarum; Urban C. S. Sjöblum, Karlskrona, all of Sweden

[73] Assignee: Landstingens Inkopscentral Lic, Ekonomisk Forening, Solna, Sweden

[21] Appl. No.: 790,910

[22] Filed: Apr. 26, 1977

[30] Foreign Application Priority Data

Apr. 28, 1976 [SE] Sweden .................... 7604885

[51] Int. Cl.$^2$ .................... A61F 1/02; A61F 1/08
[52] U.S. Cl. .................... 3/19; 3/21
[58] Field of Search .................... 3/17–21; 128/DIG. 15

[56] References Cited

U.S. PATENT DOCUMENTS

| | | | |
|---|---|---|---|
| 37,282 | 1/1863 | Engelbrecht et al. | 3/17 R X |
| 1,071,149 | 8/1913 | Erickson | 3/17 R |
| 1,211,222 | 1/1917 | Pilling et al. | 3/17 R |
| 2,634,424 | 4/1953 | O'Gorman | 3/20 |
| 3,232,289 | 1/1966 | Zimmerman | 128/DIG. 15 |
| 3,459,179 | 8/1969 | Olesen | 3/19 UX |
| 3,889,301 | 6/1975 | Bonner, Jr. | 3/20 |

*Primary Examiner*—Ronald L. Frinks
*Attorney, Agent, or Firm*—Cushman, Darby & Cushman

[57] ABSTRACT

A prosthesis for an amputated lower leg consisting of an upper part attachable to the remaining lower leg stump, this upper part being attached to an under part provided with an artificial foot. The upper part has a cup-shaped bottom portion which at a number of places along its circumference merges into upwardly directed flexible strips of such lengths that when the leg stump is placed between them they extend up along the leg stump and thigh, the bottom portion and strips forming a holder fitting, with an approximately predetermined and relatively large play, around the bandaged leg stump itself so that this play can be filled with a supporting structure around the leg stump. This structure takes the form of an envelope or cushion containing a large number of small plastic balls, said cushion being airtight but connectable to the surrounding atmosphere by a closable hose or the like, whereby the cushion, formless in an air-filled condition, can be placed round the leg stump and thigh, and formed to fit in the holder before the cushion is evacuated to form a relatively rigid shell, whereafter it is intended to clamp fast the flexible strips against the rigid shell by at least one tension band which is tightened around the strip, at least in the area about the thigh.

4 Claims, 5 Drawing Figures

U.S. Patent  Dec. 12, 1978  Sheet 1 of 3  4,128,903

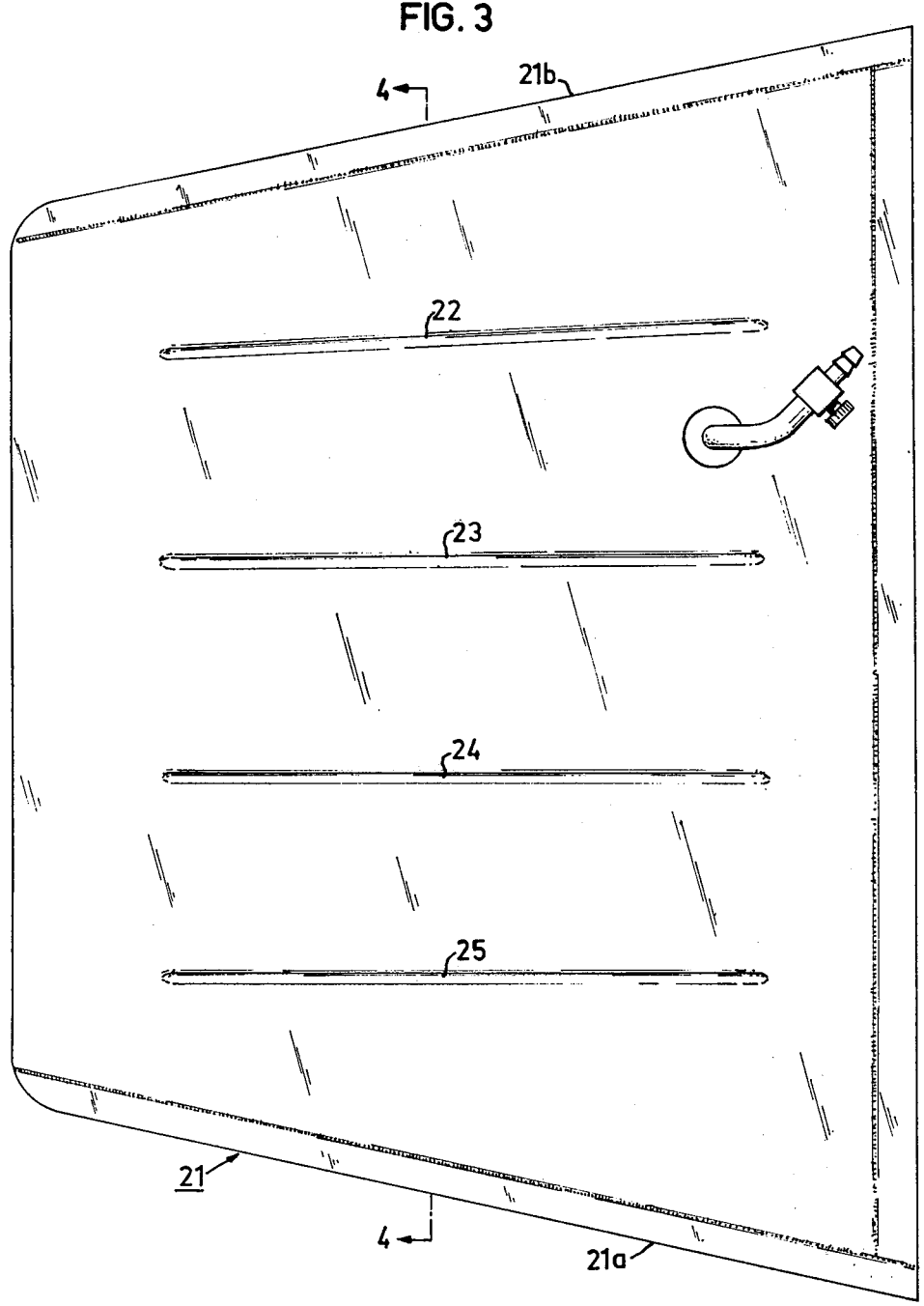

TEMPORARY WALKING AID FOR USE AFTER LOWER LEG AMPUTATIONS

The present invention relates to artificial limbs or prostheses for the lower leg, which are intended for fitting to the remaining leg stump after a lower leg amputation.

At present it is necessary to reckon with 3 to 4 months' bandaging of the leg stump before it allows taking a cast to make up a final prosthesis. The delivery time for a prosthesis made from a casting is at present 1 to 2 months, and this means that the patient can be without an artificial limb for up to 6 months after the operation. This long waiting time causes substantial risks for debilitation as well as psychic depression, in spite of the patient receiving continuous physiotherapy during this time.

With present aids it is usual that the patient must wait about 2 months after amputation of the lower leg before it is possible to take a first plaster cast for making up a first artificial limb. This artificial limb can, however, usually only be used about 2 months, since the wound swelling has then gone down so much that the prosthesis does not fit satisfactorily any more. It is then necessary to take a new plaster cast to make a second prosthesis. The present technique of taking a plaster cast of the leg stump and manufacturing a prosthesis from it thus causes substantial drawbacks for the patient and involves an important cost for manufacturing of two prostheses.

The object of the present invention is therefore, to provide a lower leg prosthesis which can form a preliminary walking aid as early as possible after amputation. Walking ability would thereby be retained to a greater extent than up to now, bleeding in the operated leg would probably not be worsened in most cases, operational edema would be less pronounced and desired atrophy of the stump would set in quicker, while at the same time the psychic strain of the operation trauma could be reduced considerably. These advantages would be of great worth, especially with regard to older persons and diabetics.

These advantages are achieved with a lower leg prosthesis which, according to the invention, has the distinguishing features set forth in the accompanying claims.

The lower leg prosthesis according to the invention is put together in a known way from an upper part joined to a lower part, the upper part being attachable to the remaining lower leg stump and the lower part being provided with an artificial foot suitably adjustable in height, and adjustable sideways by turning. According to the invention this upper part is made with a cup-shaped bottom portion, merging at a number of places along its periphery into upwardly directed flexible strips of such lengths that when the leg stump is placed in the upper part, the strips will extend upwards along the leg stump and along at least part of the length of the thigh. The bottom portion and the strips thereby form a holder which with an approximately predetermined relatively large play fits around the bandaged leg stump. The play is, however, taken up with the help of a supporting envelope enclosing the bandaged leg stump, this envelope consisting of an airtight cushion containing plastic balls. After being formed about the bandaged leg stump for suiting the leg stump with cushion to the holder, the envelope is evacuated to form a relatively rigid shell. The strips are then fastened against this shell with at least one tensioning band, suitably a band with the teasel type of fastener which is drawn tight about the strips up on the thigh. The upper part with bottom portion and strips can be manufactured in glass fibre reinforced plastic in a relatively cheap way, with an attachment for the lower part of the prosthesis moulded into the bottom portion.

The lower leg prosthesis according to the invention only needs to be manufactured in a few standard sizes, which can always be available at an orthopedic/surgical clinic in the required number. As is apparent from the above, a suitable standard size is selected and suited to the amputated leg in question, with the help of the evacuatable cushion or envelope containing the plastic balls. In this way each artificial limb can be reused, resulting in considerable savings in cost in relation to artificial limbs used up to now.

Since the lower leg prosthesis acccording to the invention is formed to take support up on the thigh, a maximum reduction of the load on the stump end is obtained, and at the same time it is possible, by adjusting the shape of the cushion before it is evacuated to form a stiff shell, to provide well-adjusted compression around the stump. The artificial leg according to the invention is made without any joint for the knee, which further reduces the strain on the stump end and facilitates walking for the patient. Since the artificial leg according to the invention is to advantage moulded in plastic, its weight will be comparatively small, which also facilitates its use and lessens the load on the leg. By releasing the tension band or bands, it is easy to remove the bottom portion with the strips from the cushion and then take away the cushion for inspecting the wound, whereafter the artificial leg can once again be fitted simply and quickly.

Tests carried out with the lower leg prosthesis according to the invention have shown that it is already possible, two or three weeks after amputation, to give the patient a temporary lower leg prosthesis according to the invention, because the prosthesis enables the large reduction of load on the stump end as mentioned above. As the wound swelling goes on, the cushion can be reshaped so that the desired fit is maintained to the strips of the prosthesis. If required, it is naturally possible to exchange the cushion for a thicker or a thinner one also.

The prosthesis according to the invention thus makes it possible to use one and the same prosthesis from an early date after the amputation and right up to trying out the final prosthesis of conventional design, and until the delivery of this prosthesis.

The number of strips can vary. Within the perview of the invention it is possible to use two relatively wide strips. However, it is usually more suitable to make the prosthesis with four strips, whereof one is in front and one behind the leg, the remaining two being on either side thereof. Since the strips are resiliently flexible, it is easy to bend them into engagement against the supporting structure formed by the cushion.

Apart from the extremely large advantage that the patient can already walk with the prosthesis according to the invention two or three weeks after the operation, instead of having to wait about two months, the number of care days will be considerably reduced, since the prosthesis according to the invention enables more rapid healing, as well as fitting the final prosthesis at a considerably earlier stage than has been possible up to now.

These and other distinguishing features and advantages of the invention will now be explained more closely, while referring to the appended drawings showing an embodiment of a lower leg prosthesis according to the invention.

Figure 2:
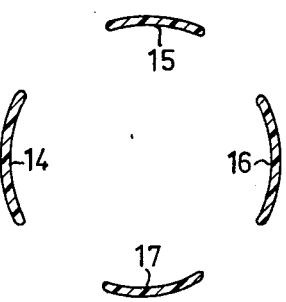
Figure 5:
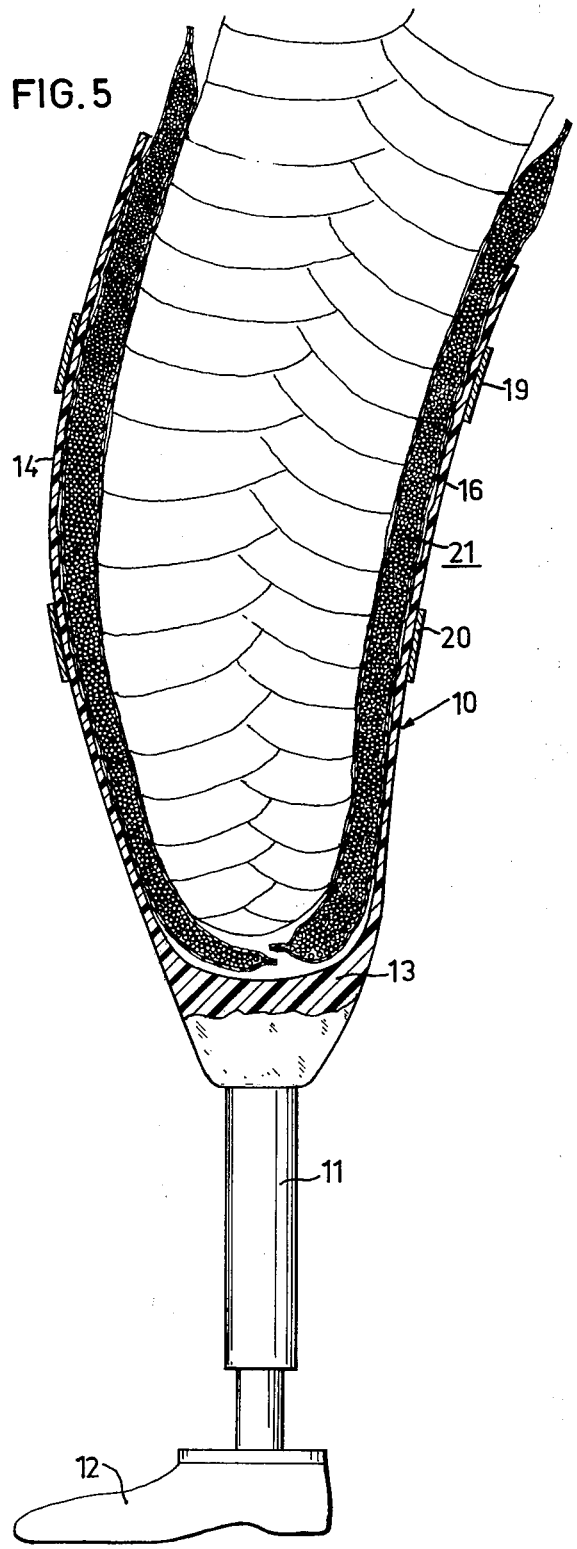

FIG. 1 is a side view of a lower leg prosthesis according to the invention, before it is fitted to a leg stump wound provided with a supporting envelope according to the invention, FIG. 2 is a section along the line 2—2 in FIG. 1, FIG. 3 is an evacuatable flat plastic cushion or envelope containing a large number of small plastic balls, FIG. 4 is a section along the line 4—4 in FIG. 3 and FIG. 5 shows schematically in section an amputated lower leg, surrounded by an evacuated cushion according to FIG. 3 and fastened between the strips of the prosthesis.

The prosthesis consists of an upper part 10 which at its lower end is carried by an under part in the form of a telescopic tube 11, adjustable and lockable to different lengths and degrees of turning, and provided with an artificial foot 12.

The upper part is made in one piece from glass fibre reinforced plastic and has a cup-shaped bottom portion 13, which at four approximately uniformly distributed places about its circumference merges into four upwardly directed resiliently flexible strips 14,15,16,17. The strips are suitably somewhat arcuate in cross section as is apparent from FIG. 2.

The strips have a substantially constant wall thickness. The spaces between the strips suitably have a width which is approximately the same as the width of the strips. Since the strips are resiliently flexible, they can be bent outwardly or inwardly for easy adjustment to a body which is accommodated in the holder formed by the bottom portion and the strips.

The bottom part has a comparatively thick bottom in which there is molded an attachment 18 for the telescopic tube 11.

An upper and a lower tension band 19 and 20 are attached to the rear strip 16. To firmly attach the strips, the bands are wound around them and drawn tight for fastening with Velcro ® or teasel-type fastening or bands at their mating ends.

Associated with the prosthesis according to the invention there is also a cushion or envelope of the design shown in FIGS. 3 and 4, for example. The cushion 21 is relatively flat and has such width and length that it can be placed around the leg stump and a portion of the thigh so that the side edges 21a,21b of the cushion overlap each other. By means of longitudinal welding seams 22,23,24,25 the cushion is divided into a number of compartments communicating with each other and containing a large number of small plastic balls having a size of 1-2 mm in diameter. The cushion is made from plastic film and is airtight. A hose with a closeable connecting nozzle is used to allow air into the cushion and for evacuating air from it, by means of a hand-operated suction pump, for example.

When the nozzle is open, the cushion is filled with air for providing an easily formable body. In this condition the cushion is placed around the bandaged leg stump. The cushion is then shaped to fit on the inside of the strips of the prosthesis. The shaping is carried out by distributing the plastic balls so that the cushion is made thicker or thinner at different places, allowing it to fit comparatively accurately on the inside of the strips, with the lower end of the leg stump protected by the cushion engaging only lightly against the bottom of the bottom portion 13 or completely free from it. Thereafter the cushion is evacuated and the nozzle is closed. On being evacuated, the cushion stiffens to a relatively rigid shell which takes up the play between the strips and the leg stump to make a good fit. In certain cases, the strips are bent outwards somewhat by the cushion, but they are once again drawn into accurate engagement against the rigid cushion when the tension bands 19,20 are tightened up. In certain cases it is sufficient with the upper tension band which tightens the strips against the thigh. The weight of the patient will thus be transferred via the relatively rigid cushion to the strips and further to the lower part of the prosthesis, thus reducing the load on the end of the leg stump to a considerable degree.

What is claimed is:

1. A prosthesis for an amputated lower leg comprising an upper part attachable to the remaining lower leg stump and a supporting cushion structure, this upper part being attached to an under part provided with an artificial foot, characterized in that the upper part has a cup-shaped bottom portion which at a number of places along its circumference merges into upwardly directed flexible strips of such lengths that, when the leg stump is placed between them, they extend up along the leg stump and thigh, the bottom portion and stips forming a holder adapted to fit, with an approximately predetermined and relatively large play, around the bandaged leg stump itself so that this play can be filled with said supporting structure around the leg stump, said structure taking the form of an envelope or cushion containing a large number of small plastic balls, said cushion being airtight but connectable to the surrounding atmosphere by a closeable hose or the like whereby the cushion, formless in an air-filled condition, can be placed around the leg stump and thigh, and formed to fit in the holder before the cushion is evacuated to form a relatively rigid shell, whereafter it is intended to clamp fast the flexible strips against the rigid shell by at least one tension band which is tightened around the strips, at least in the area about the thigh.

2. A prosthesis as claimed in claim 1, characterized in that the number of strips is four, with one strip for engaging on the front of the leg, one at the back of the leg and one strip on either side of the leg.

3. A prosthesis as claimed in claim 1, characterized in that the upper part is formed in one piece from a resilient material, suitably such as glass fibre reinforced plastic.

4. A prosthesis as claimed in claim 1, characterized in that said at least one tension band is provided with teasel-type or Velcro ® bands enabling continuous adjustment of the tensioning force.

* * * * *